US008273392B2

(12) United States Patent
Ho et al.

(10) Patent No.: US 8,273,392 B2
(45) Date of Patent: Sep. 25, 2012

(54) FERMENTED FROZEN DESSERT

(75) Inventors: Dac Thang Ho, Le Mont S/Lausanne (CH); Christelle Schaffer-Lequart, Mezieres (CH); Steffen Dose, Bakersfield, CA (US); Sylvie Tournade, Caen (FR)

(73) Assignee: Nestec S.A., Vevey (CH)

( * ) Notice: Subject to any disclaimer, the term of this patent is extended or adjusted under 35 U.S.C. 154(b) by 854 days.

(21) Appl. No.: 12/299,254

(22) PCT Filed: Mar. 29, 2007

(86) PCT No.: PCT/EP2007/053022
§ 371 (c)(1),
(2), (4) Date: Oct. 31, 2008

(87) PCT Pub. No.: WO2007/128625
PCT Pub. Date: Nov. 15, 2007

(65) Prior Publication Data
US 2009/0186124 A1    Jul. 23, 2009

(30) Foreign Application Priority Data
May 3, 2006 (EP) .................................... 06113444

(51) Int. Cl.
*A23C 9/12* (2006.01)
*C12N 1/20* (2006.01)

(52) U.S. Cl. .............. 426/42; 426/34; 426/43; 426/564; 426/565; 426/580; 435/252.9

(58) Field of Classification Search ............ 426/34, 426/42, 43, 564, 565, 580; 435/252.9
See application file for complete search history.

(56) References Cited

U.S. PATENT DOCUMENTS

| | | | |
|---|---|---|---|
| 4,293,573 A | 10/1981 | Bradley, Jr. et al. | 426/43 |
| 4,357,423 A | 11/1982 | Cox et al. | 435/101 |
| 2003/0186392 A1 | 10/2003 | Trempy et al. | 435/101 |

FOREIGN PATENT DOCUMENTS

| | | |
|---|---|---|
| DE | 196 10 672 A1 | 9/1997 |
| EP | 1 430 785 A2 | 6/2004 |
| EP | 1 180 329 B1 | 10/2005 |
| JP | 9 084 521 | 3/1997 |
| JP | 2001 258 478 | 9/2001 |
| JP | 2005 278 638 | 10/2005 |
| WO | WO 94/12656 | 6/1994 |
| WO | WO 03/102204 A2 | 12/2003 |

OTHER PUBLICATIONS

International Search Report PCT/EP2007/053022 Dated Jul. 10, 2007.
S.M. Schellhaass, *Characterization of Exocellular Slime Produced by Bacterial Starter Cultures Used in the Manufacture of Fermented Dairy Products*, Dissertation Abstracts International, Order No. DA 8329584, Univ. of Minnesota, Minneapolis, Minnesota, vol. 44, No. 9, 1984 (XP008069219).
S. H. Hong et al., *Natural Exopolysaccharides Enhance Survival of Lactic Acid Bacteria in Frozen Dairy Desserts*, Jun. 2001, Journal of Dairy Science, American Dairy Science Association, vol. 84, No. 6,; pp. 1367-1374 (XP-001043660).
L. Jolly et al., *Exploiting Exopolysaccharides From Lactic Acid Bacteria*, 2002, Antonie Van Leeuwenhoek, vol. 82, pp. 367-374, Kluwer Academic Publishers (XP-002400077).
S.J. Hess et al., *Rheological Properties of Nonfat Yogurt Stablilized Using Lactobacillus Delbrueckii ssp. Bulgaricus Producing Exopolysaccharide or Using Commercial Stabilizer Systems*, Feb. 1997, Journal of Dairy Science, American Dairy Science Association, vol. 80, No. 2, pp. 252-263, (XP 000680757).
P.S. Christiansen, *The Use of Ropy Milk As Stabilizer in the Manufacture of Ice Cream*, 1999, Milchwissenschaft, vol. 54, No. 3, pp. 138-140, VV Gmbh, Volkswirtschaftlicher Verlag, Munchen, Germany (XP000825735).

*Primary Examiner* — Leslie Wong
(74) *Attorney, Agent, or Firm* — Winston & Strawn LLP

(57) ABSTRACT

The present invention relates to frozen desserts which can be free of additives. It also pertains to a process for the manufacture of such frozen dessert which process includes the step of fermenting milk proteins with micro-organisms yielding hetero-exopolysaccharides, and thus avoiding the use of additives such as thickeners or stabilizers.

19 Claims, 1 Drawing Sheet

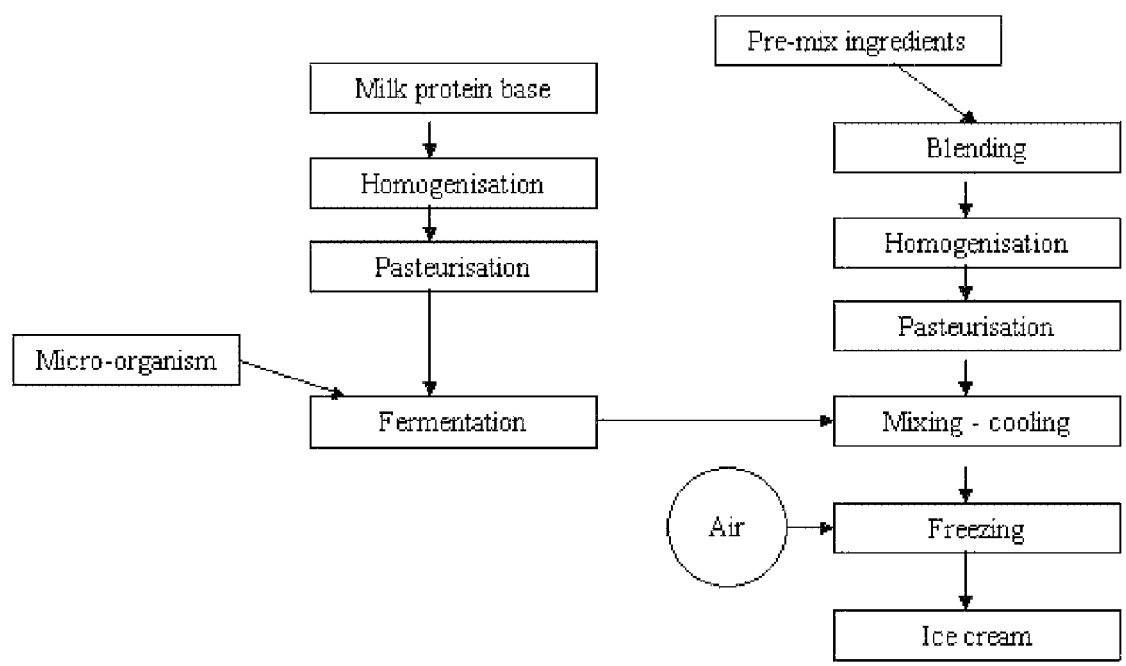

FERMENTED FROZEN DESSERT

This application is 317 filing of International Patent Application PCT/EP2007/053022 filed Mar. 29, 2007.

FIELD OF THE INVENTION

The present invention relates to frozen desserts which can be free of additives. It also pertains to a process for the manufacture of such frozen dessert comprising the step of fermenting milk proteins with micro-organisms yielding hetero-exopolysaccharides, and thus avoiding the use of additives such as thickeners and/or stabilisers.

BACKGROUND ART

Additives used in the field of frozen desserts comprise stabilisers, emulsifiers, thickening agents, flavouring agents etc. These additives have to be declared in Europe on the label or packaging as "E-numbers". Endeavours to manufacture frozen desserts free from additives are increasing with the aim of providing consumers with an "all natural" frozen dessert having a clean label.

Due to their stabilising/emulsifying/thickening properties, the exopolysaccharides (EPS) are being used in the field of frozen dessert. These are compounds which are naturally produced by certain strains of micro-organisms.

For instance, WO 94/12656 (Quest International B.V.) describes new *Lactobacillus* strains which are capable of producing exopolysaccharide. These are used mainly for their thickening and/or emulsion-stabilising properties.

EP 1 430 785 A2 (Yogurtal S.p.A.) discloses an ice-cream yogurt which is free of additives normally used in ice-cream production. The frozen yogurt contains live micro-organisms generated by a culture capable of also producing exopolysaccharides.

The problem encountered when using micro-organisms such as lactic acid bacteria is that the pH of the final product may be too low for frozen dessert applications.

In EP 1 180 329 B1 (Unilever), additive-free ice cream confections are produced by fermenting a milk composition with a homo-exopolysaccharide producing micro-organisms. The fermentation is stopped before the pH reaches a value below 5.5.

There thus still remains a need to provide in a simple way, a technology that allows producing frozen desserts with low acidity and without needing additives.

SUMMARY OF THE INVENTION

Accordingly, this object is achieved by means of the features of the independent claims. The dependent claims further develop the central idea.

The invention proposes, in a first aspect, a frozen dessert comprising hetero-exopolysaccharides and micro-organisms selected from a strain capable of synthesising the hetero-exopolysaccharides present in the dessert.

In a second aspect of the invention, a process for the manufacture of a frozen dessert comprises the steps of:
 a. Fermenting a milk-protein base comprising at least 20% milk-solids non-fat (MSNF) by weight with a lactic acid bacteria under anaerobic conditions
 b. Cooling said fermentation mix
 c. Providing a homogenised, pasteurised and cooled pre-mix comprising at least a dairy component
 d. Cold mixing the fermentation mix with the cooled pre-mix
 e. Ageing, freezing and aerating the final mix.

The use of hetero-exopolysaccharides comprising units of glucose and galactose for stabilising frozen desserts against heat shock falls under a third aspect of the present invention.

FIGURES

FIG. 1 is a flow-chart representing ice-cream preparation. The flow-chart illustrates on the left-hand side the steps required to obtain the fermentation mix. On the right-hand side, preparation of the pre-mix is illustrated. Mixing both fermentation mix and pre-mix yields the ice cream of the present invention.

DETAILED DESCRIPTION OF THE INVENTION

The present invention relates to frozen desserts which comprise hetero-exopolysaccharides (hetero-EPS) and micro-organisms selected from a strain capable of synthesising hetero-exopolysaccharides, especially from mono- or disaccharides.

The micro-organisms comprised in the frozen dessert of the present invention are preferably selected strains of lactic acid bacteria selected from the group of *Lactobacillus, Lactococcus, Streptococcus*. Lactic acid bacteria capable of synthesising hetero-exopolysaccharides comprise, for instance, *Lactobacillus delbrueckii* subsp. *bulgaricus, Lactobacillus delbrueckii* subsp. *lactis, Lactococcus lactis* subsp. *cremoris, Lactococcus lactis* subsp. *lactis, Streptococcus thermophilus* etc. Preferably, the lactic acid bacteria is selected from *Lactobacillus delbrueckii* subsp. *bulgaricus* NCC 526 (deposition number CNCM I-3600), *Lactobacillus delbrueckii* subsp. *lactis* NCC 2812 (deposition number NCIMB 700860) or mixtures thereof. Preferably, the micro-organism present in the frozen dessert of the present invention is viable.

Hetero-exopolysaccharides are composed of different sugar moieties with repeating motifs. These are secreted by the micro-organism during growth and stationary phases.

Preferably, the hetero-exopolysaccharides comprised in the frozen dessert of the present invention comprise units of glucose and galactose. Additionally, they may comprise units of rhamnose. When the hetero-exopolysaccharides are composed of glucose and galactose, these are preferably present in a ratio ranging from (2 to 4):(1 to 3) respectively. More preferably it is 3:2 (glucose:galactose).

When rhamnose is additionally present, the hetero-exopolysaccharides preferably comprise glucose, galactose and rhamnose in a ratio of (2 to 4):(4 to 6):(1 to 3) respectively. More preferably it is 3:5:1 (glucose:galactose:rhamnose).

The advantage of having hetero-exopolysaccharides producing micro-organisms in the frozen dessert of the invention is that the hetero-exopolysaccharides produced enable a greater diversity in terms of texture compared to homo-exopolysaccharides (homo-EPS) for instance. Furthermore, desirable textural properties are attained in the frozen product at much lower concentration than with other exopolysaccharides. For instance, a concentration of 0.05% or less of hetero-exopolysaccharides in the final product is sufficient to impart desirable textural properties and stability to the frozen dessert. This offers the advantage that no stabilisers, thickening agents need to be added to the frozen dessert.

Additionally, hetero-exopolysaccharides comprising units of glucose and galactose may be used for stabilising frozen desserts against heat shock. The hetero-exopolysaccharide may further comprise units of rhamnose. When the hetero-exopolysaccharides are composed of glucose and galactose, these are preferably present in a ratio ranging from (2 to 4):(1 to 3) respectively. More preferably it is 3:2 (glucose:galactose). When rhamnose is additionally present, the hetero-exopolysaccharides preferably comprises glucose, galactose and rhamnose in a in a ratio of (2 to 4):(4 to 6):(1 to 3) respectively. More preferably it is 3:5:1 (glucose:galactose:rhamnose).

Thus the frozen dessert of the present invention may withstand temperature fluctuations without losing textural and organoleptic properties.

The frozen dessert of the present invention can be aerated to any overrun, depending on the application. Preferably the overrun will be between 50% and 250%, most preferably it is 100%.

The frozen dessert of the present invention is characterised by a high content in milk solids non-fat (MSNF). Preferably, the frozen dessert will contain at least 20%, more preferably at least 25%-30% MSNF. A high MSNF content presents the advantage that the MSNF may act as a buffer in the product, thus reducing the perceived acidity of said product. Indeed, the invention allows to produce, if desired, frozen desserts having a low acidity such as e.g. a pH value of between 5 and 6, preferably 5.5, without perceived acidity. This is in contrast to methods which inevitably result in products with perceivable acidity, which can be tolerated e.g. for frozen yogurt preparations which generally have a lower pH and wherein the acidity is perceivable.

The frozen dessert of the invention may be any frozen dessert such as, for example, mellorine, milk-shake, smoothy, soft-ice, sorbet etc. Preferably, it is ice cream.

The present invention provides a process for the manufacture of a frozen dessert comprising firstly the step of fermenting a milk-protein base comprising at least 20% MSNF by weight with a lactic acid bacteria. Preferably, the milk-protein base comprises at least 80% casein. Thus, the milk solids non-fat is preferably skimmed milk powder. Preferably, the milk-protein base is sucrose-free.

In a preferred embodiment of the present invention, the milk protein base may be subjected to a low-heat treatment prior to fermentation. This will have the advantage that the viscosity of the fermentation mix is increased. Furthermore, this will provide better resistance to temperature fluctuation cycles while minimising perceived acidity in the final product. By "low-heat treatment" is meant subjecting the milk proteins to temperatures between 80° C. and 90° C. for a period of time between 1 minute and 20 minutes. Preferably, the low-heat treatment is carried out at 85° C. for 15 minutes.

The fermentation step is carried out under anaerobic conditions. Preferably, the fermentation step is performed for at least 15 hours. The temperature of fermentation is set such that optimal growth of the microbial strain is achieved. This is dependent on the micro-organism used, but will generally be between 30 and 40° C. During the fermentation step, hetero-exopolysaccharides are produced in situ.

In a second step, the fermentation mix is cooled. Preferably the cooling is carried out to less than 10° C., more preferably to 4° C. This has the effect of stopping the fermentation, whilst keeping the micro-organisms used in the fermentation viable. The usual pasteurisation step in order to stop fermentation is not necessary as—contrary to the micro-organisms producing homo-EPS—the main step of hetero-EPS production takes place inside the cell walls of the micro-organisms such that no external enzymes have to be inactivated by heat treatment.

Separately, a pre-mix comprising at least a dairy component is prepared. Typically, the pre-mix contains cream as the dairy component. It may further comprise egg yolk and sugars. The sugars used can be any sugar used in the field of frozen desserts. Preferably, the sugars are selected glucose, sucrose, fructose, inverted sugars, glucose syrup, corn syrup, lactose etc. Typically, the ingredients of the pre-mix and water are homogenised and pasteurised. The pasteurisation preferably takes place at 85° C. for 30 s, before cooling to less than 10° C., preferably to 4° C.

The fermentation mix and the pre-mix are then mixed at low temperature, preferably at 4° C. These are blended such that the pre-mix is contained in the final mix in an amount of about 35-45%. The blend is then aged for at least 15 hours, aerated and frozen. Aeration may be carried out to an overrun of about 100%.

Frozen dessert obtainable by the present inventive process offer the advantage of having desirable organoleptic/textural/stability properties without the need for additives. Preferably the frozen dessert thus obtainable is ice cream.

The present invention is further illustrated by way of non-limiting examples.

EXAMPLES

Fermentation of milk: The first stage fermentation of milk was done separately (shown in left-hand side boxes in FIG. 1).

In a first step, the dissolution of skimmed milk powder in water was done in a 75-L jacketed tank to the desired dried matter (e.g. TS=29%). A 2-stages homogenisation at 65° C. and 140/40 bars was effected in the medium before fermentation. The product was pasteurised continuously at 85° C. for a residence time of 30 sec and cooled to 5° C. Before inoculation the medium was heated to the desired growth temperature of the starter (e.g. 40° C. for thermophilic strains). The volume of the starter was 5% based on the volume of medium. The fermentation was effected in a close vessel with no stirring. After 15 h, the fermentation was stopped by cooling the fermented milk with chilled water at 4° C. before mixing with the "pre-mix" part described below.

Preparation of "Pre-Mix" (Shown in the Right-Hand Side Boxes in FIG. 1)

A mixing of sucrose, invert sugar, glucose syrup ingredients and egg yolk was done in a separate tank containing water. Cream was then added and the mix was homogenized at 65° C., in 2-stages at 140/40 bar, with an APV system unit at a flow rate of 60 l/h. The product was then pasteurised at 85° C. for 30 sec. cooled to 4° C. before mixing with the cooled fermented milk.

Preparation of Ice Cream Mix:

The fermented milk and the pre-mix were blended together at a right percentage and aged overnight (>15 h) at 4° C. The ice cream mix was pumped through a mono pump at a flow rate of 25 l/h. The Mono pump was found better than piston pump to handle viscous products. The mix was cooled to −6° C. in a Hoyer freezer MF50, injected with air and whipped with a scraper blade at 500 rpm. The amount of air was adjusted to achieve 100% overrun. The overrun is defined as the percentage of: ml of frozen ice cream−ml of the ice cream mix)/ml of ice cream mix. The ice cream was flowing out continuously of the freezer at a back pressure of 2 bars and was filled in 75 ml plastic cups and further frozen down to −38° C. in a batch freezer.

Note that any group of substances listed above is explicitly also encompassing any combination of one or more members of the group.

The article "a" does not constitute a limitation as to the number, but has to be understood as "one or more".

The invention claimed is:

1. An edible composition comprising a frozen dessert that includes at least 20% milk solids non fat, with a pH comprised between 5 and 6, and hetero-exopolysaccharides in an amount sufficient to impart textural properties and stability to the frozen dessert, wherein the frozen dessert is free of stabilizers or thickening agents, wherein the hetero-exopolysaccharides are synthesized in situ in the dessert by contact of micro-organisms with mono or di-saccharides, wherein the micro-organisms are selected from at least one strain capable of synthesizing the hetero-exopolysaccharides in the dessert, and no stabilizers or thickening agents are present in the dessert, and wherein the hetero-exopolysaccharides comprise units of glucose, galactose and rhamnose present in a ratio of from (2 to 4):(4 to 6):(1 to 3), respectively, and in an amount sufficient to stabilize the frozen dessert against heat shock.

2. The composition of claim 1, wherein the micro-organisms are viable strains of lactic acid bacteria selected from the group of *Lactobacillus, Lactococcus*, or *Streptococcus*.

3. The composition of claim 2, wherein the lactic acid bacteria are selected from *Lactobacillus delbrueckii* subsp. *bulgaricus* (CNCM I-3600), *Lactobacillus delbrueckii* subsp. *lactis* (NCIMB 700860) or mixtures thereof.

4. The composition of claim 1, having an overrun in the range of 50-250%, at least 20% milk total solids and a pH of between 5 and 6.

5. The composition of claim 1, wherein the frozen dessert is an ice cream.

6. A process for the manufacture of a frozen dessert according to claim 1, which comprises:
    fermenting a milk-protein base comprising at least 20% non-fat milk solids by weight with a hetero-exopolysaccharide producing lactic acid bacteria under anaerobic conditions to form a fermentation mix that includes hetero-exopolysaccharides comprising units of glucose, galactose and rhamnose in a ratio ranging from (2 to 4):(4 to 6):(1:3), respectively;
    cooling the fermentation mix;
    providing a homogenized, pasteurized and cooled pre-mix comprising at least one dairy component;
    mixing the cooled fermentation mix with the cooled pre-mix to form a frozen dessert mix; and
    ageing, freezing and aerating the frozen dessert mix to form the frozen dessert.

7. The process of claim 6, wherein the non-fat milk solids comprises skimmed milk powder.

8. The process of claim 6, which further comprises preparing the milk protein base by subjecting milk proteins to a heat treatment.

9. The process of claim 6, wherein the milk protein base comprises at least 80% casein.

10. The process of claim 6, wherein the lactic acid bacteria are viable and are selected from *Lactobacillus, Lactococcus*, or *Streptococcus*, wherein the hetero-exopolysaccharides are produced in situ during preparation of the frozen dessert.

11. The process of claim 10, wherein the lactic acid bacteria are selected from *Lactobacillus delbrueckii* subsp. *bulgaricus* (CNCM I-3600), *Lactobacillus delbrueckii* subsp. *lactis* (NCIMB 700860) or mixtures thereof.

12. The process of claim 6, wherein the pre-mix comprises about 35-45% of the frozen dessert mix.

13. The process of claim 6, wherein the mixing of the cooled fermentation mix with the cooled pre-mix is carried out at about 4° C., the ageing is carried out for at least 15 hours and the aeration is carried out to an overrun of between 50% and 250%.

14. A method of stabilizing a frozen dessert against heat shock which comprises adding or forming in situ in the dessert hetero-exopolysaccharides comprising units of glucose, galactose, and rhamnose in a ratio of from (2 to 4):(4 to 6):(1 to 3) and in an amount sufficient to stabilize the frozen dessert against heat shock, wherein the frozen dessert is free of stabilizers or thickening agents.

15. *Lactobacillus delbrueckii* subsp. *bulgaricus* (CNCM I-3600).

16. An edible composition comprising a frozen dessert having a pH comprised between 5 and 6 and consisting essentially of at least 20% milk solids non fat, and hetero-exopolysaccharides in an amount sufficient to impart textural properties and stability to the frozen dessert, wherein the frozen dessert is free of stabilizers or thickening agents or other additives, wherein the hetero-exopolysaccharides comprise units of glucose, galactose and rhamnose present in a ratio of 3:5:1, respectively, and in an amount sufficient to stabilize the frozen dessert against heat shock, and no stabilizers, thickening agents or other additives are present in the dessert.

17. A process for the manufacture of a frozen dessert according to claim 16, which comprises:
    fermenting a milk-protein base that includes at least 20% non-fat milk solids by weight with a hetero-exopolysaccharide producing lactic acid bacteria under anaerobic conditions to generate, in situ, hetero-exopolysaccharides comprising units of glucose, galactose and rhamnose is in a ratio ranging from (2 to 4):(4 to 6):(1:3), respectively, and form a fermentation mix;
    cooling the fermentation mix without a separate pasteurization step to terminate fermentation;
    providing a homogenized, pasteurized and cooled pre-mix that includes at least one dairy component;
    mixing the cooled fermentation mix with the cooled pre-mix to form a frozen dessert mix; and
    ageing, freezing and aerating the frozen dessert mix to form the frozen dessert.

18. The process of claim 17 wherein the glucose, galactose, and rhamnose are present in a ratio of 3:5:1.

19. The method of claim 14 wherein the glucose, galactose, and rhamnose are present in a ratio of 3:5:1.

* * * * *